(12) United States Patent
Hendrikse et al.

(10) Patent No.: US 9,134,208 B2
(45) Date of Patent: Sep. 15, 2015

(54) SOLID PHASE MICRO EXTRACTION (SPME) VACUUM INLET

(75) Inventors: Jan Hendrikse, Whitby (CA); Vladimir Romanov, Vaughan (CA)

(73) Assignee: Smiths Detection Montreal Inc. (CA)

( * ) Notice: Subject to any disclaimer, the term of this patent is extended or adjusted under 35 U.S.C. 154(b) by 329 days.

(21) Appl. No.: 13/562,762

(22) Filed: Jul. 31, 2012

(65) Prior Publication Data

US 2014/0033835 A1    Feb. 6, 2014

(51) Int. Cl.
*G01N 1/44* (2006.01)
*H01J 49/04* (2006.01)
*G01N 1/00* (2006.01)

(52) U.S. Cl.
CPC ............. *G01N 1/44* (2013.01); *H01J 49/049* (2013.01); *G01N 2001/002* (2013.01)

(58) Field of Classification Search
CPC ............. G01N 1/44; G01N 2001/02; G01N 2001/002; H01J 49/049
USPC .............. 73/863.12, 864.81, 864.85; 250/288
See application file for complete search history.

(56) References Cited

U.S. PATENT DOCUMENTS

| | | | | |
|---|---|---|---|---|
| 3,548,188 | A * | 12/1970 | Nemeth | 49/49 |
| 6,405,608 | B1 * | 6/2002 | Lindgren et al. | 73/863.21 |
| 6,759,126 | B1 * | 7/2004 | Malik et al. | 428/391 |
| 6,815,216 | B2 * | 11/2004 | Sandra et al. | 436/178 |
| 7,270,020 | B2 * | 9/2007 | Gregory et al. | 73/864.85 |
| 7,464,614 | B2 * | 12/2008 | Harvey | 73/863.84 |
| 8,822,949 | B2 * | 9/2014 | Krechmer et al. | 49/49 |
| 2010/0011888 | A1 * | 1/2010 | Pawliszyn et al. | 73/864.11 |
| 2010/0200509 | A1 * | 8/2010 | Suh et al. | 210/670 |
| 2011/0118452 | A1 * | 5/2011 | Gjerde et al. | 530/413 |

FOREIGN PATENT DOCUMENTS

| | | | | |
|---|---|---|---|---|
| CN | 2700880 Y | * | 5/2005 | G01N 30/08 |
| CN | 1628889 A | * | 6/2005 | B01D 11/04 |
| CN | 1299793 C | * | 2/2007 | G01N 30/08 |
| CN | 101532993 A | * | 9/2009 | G01N 30/02 |
| CN | 101698519 A | * | 4/2010 | G01N 1/28 |
| CN | 101912769 A | * | 12/2010 | B01D 15/08 |
| CN | 101637668 B | * | 7/2011 | G01N 1/40 |

OTHER PUBLICATIONS

PCT International Search Report for PCT/IB2013/002088, mailed Jan. 28, 2014.*

* cited by examiner

*Primary Examiner* — Thomas P Noland
(74) *Attorney, Agent, or Firm* — Advent, LLP

(57) ABSTRACT

A sample introduction system configured for introducing analytes of a solid phase micro extraction (SPME) sample into an analytical instrument system (e.g., mass spectrometer) is described. The sample introduction system includes a pressure vessel configured with an inlet port via which a probe portion (e.g., SPME fiber) of a SPME assembly is received into a sealed volume of the pressure vessel. The probe portion of the SPME assembly is coated with an extracting phase material, the analytes being absorbed into and/or adsorbed onto the extracting phase material. The pressure vessel is configured for providing an environment in which desorption of the analytes from the extracting phase material occurs at a gaseous pressure which is substantially less than atmospheric pressure (e.g., less than 100 mTorr). The desorbed analytes are then directed to the vacuum chamber of the analytical instrument system via an outlet port of the pressure vessel.

14 Claims, 11 Drawing Sheets

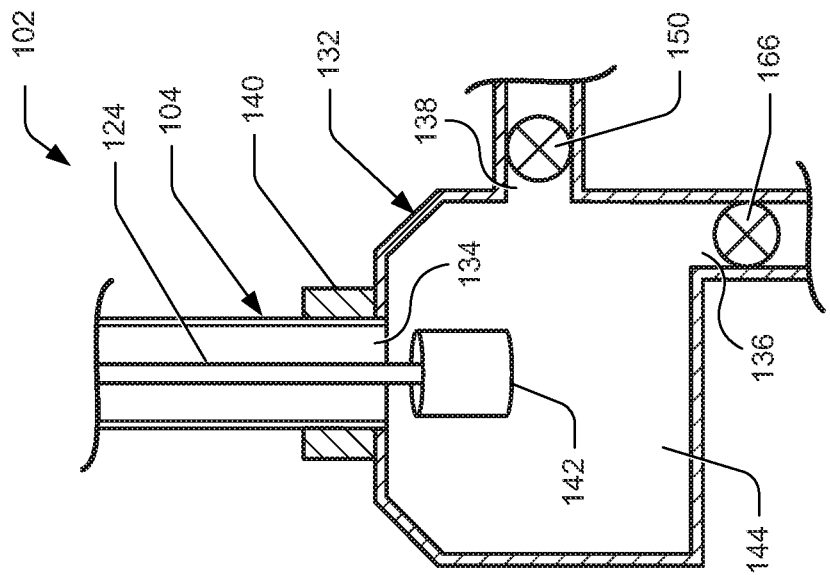
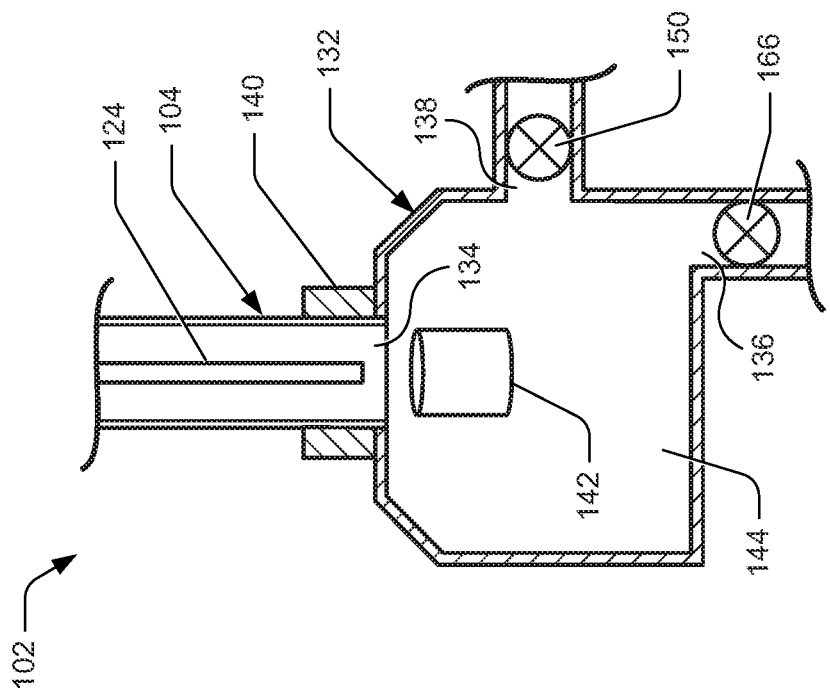

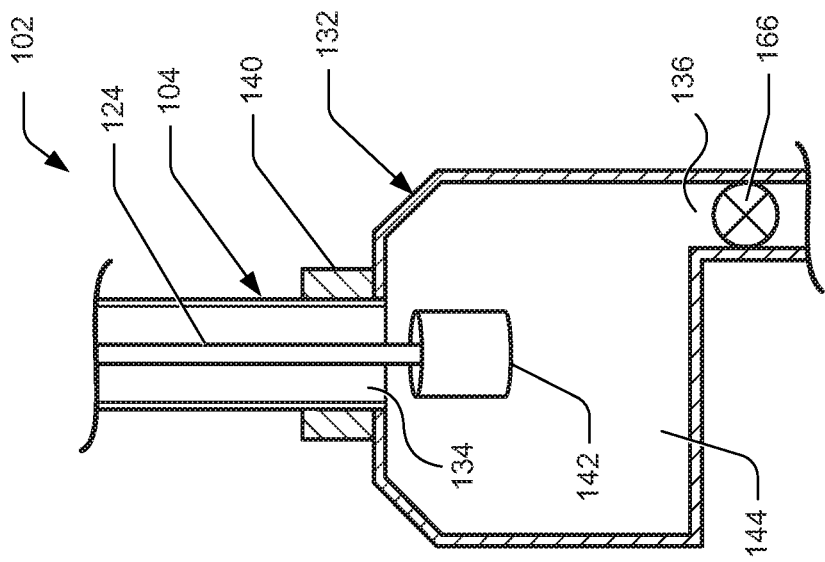
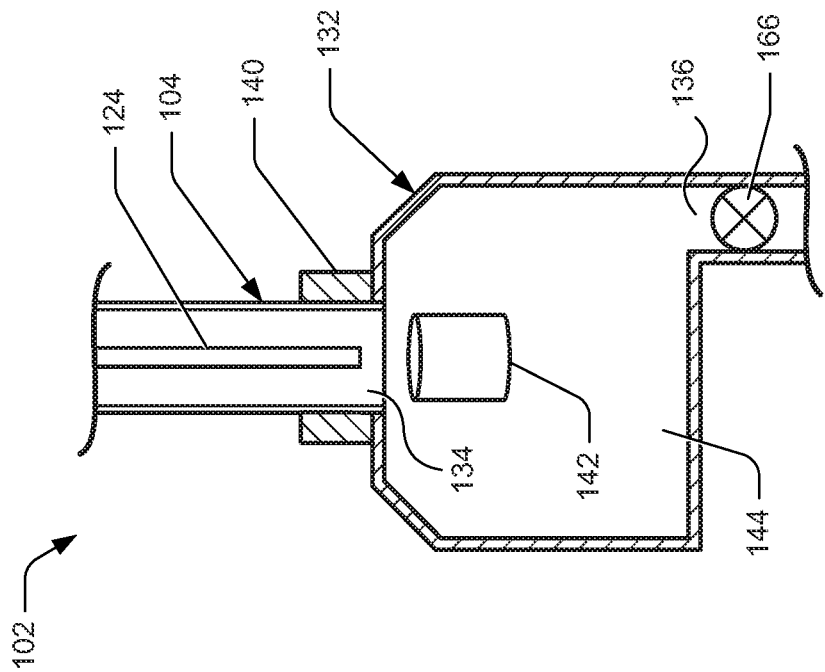

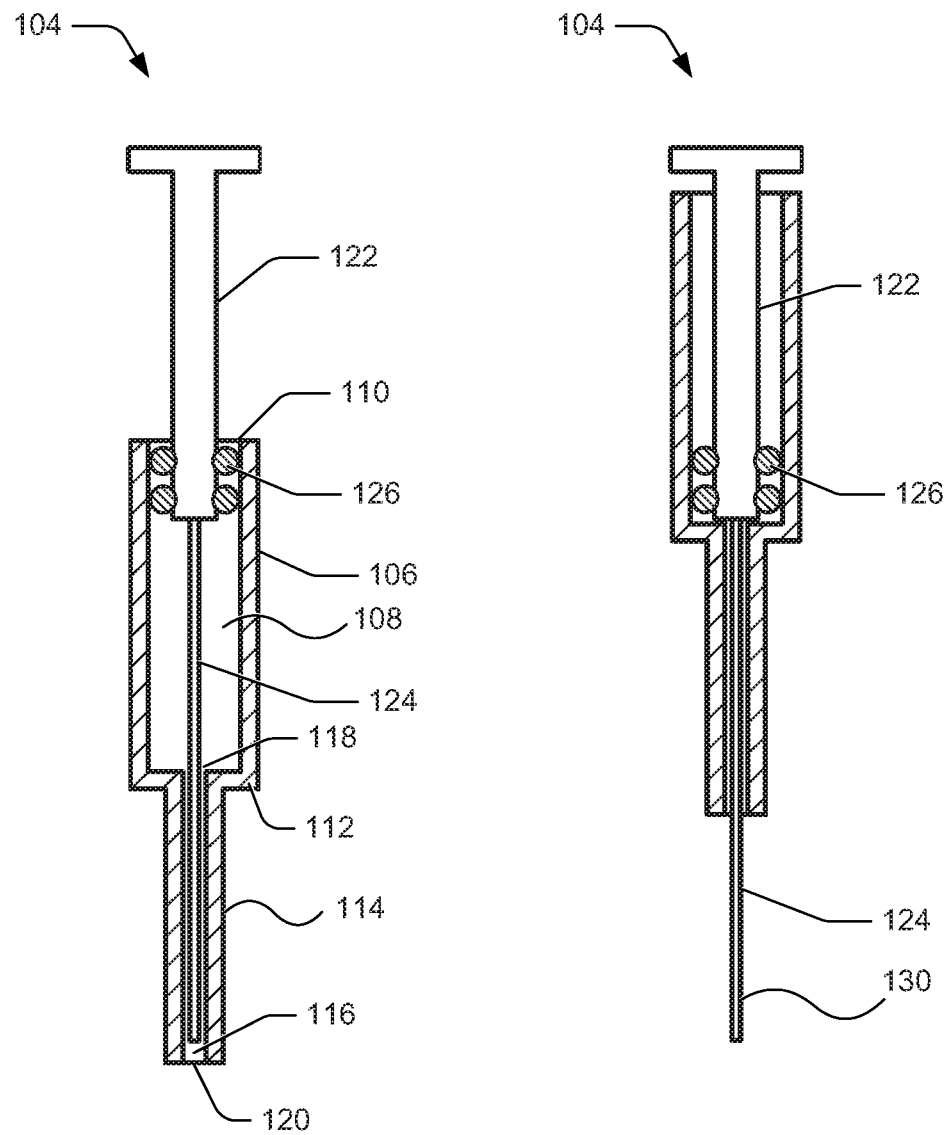

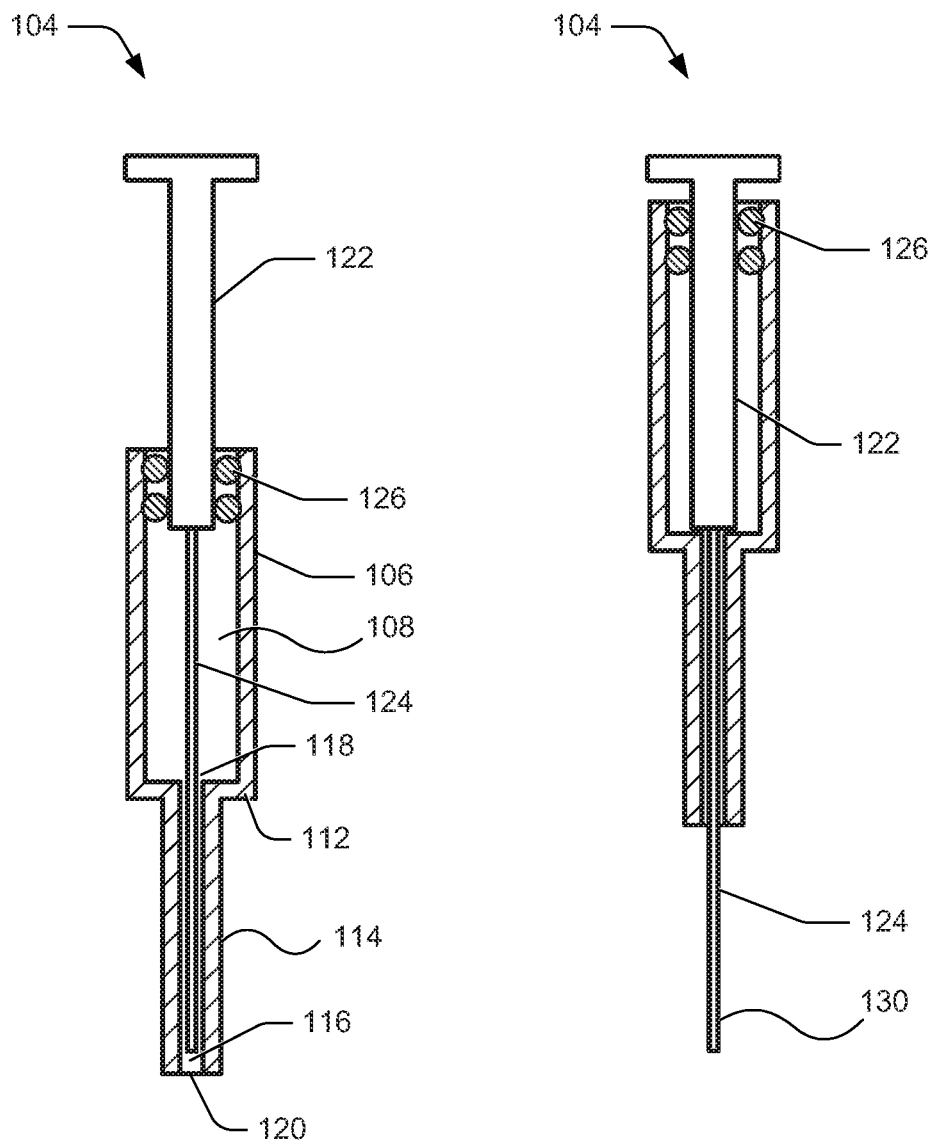

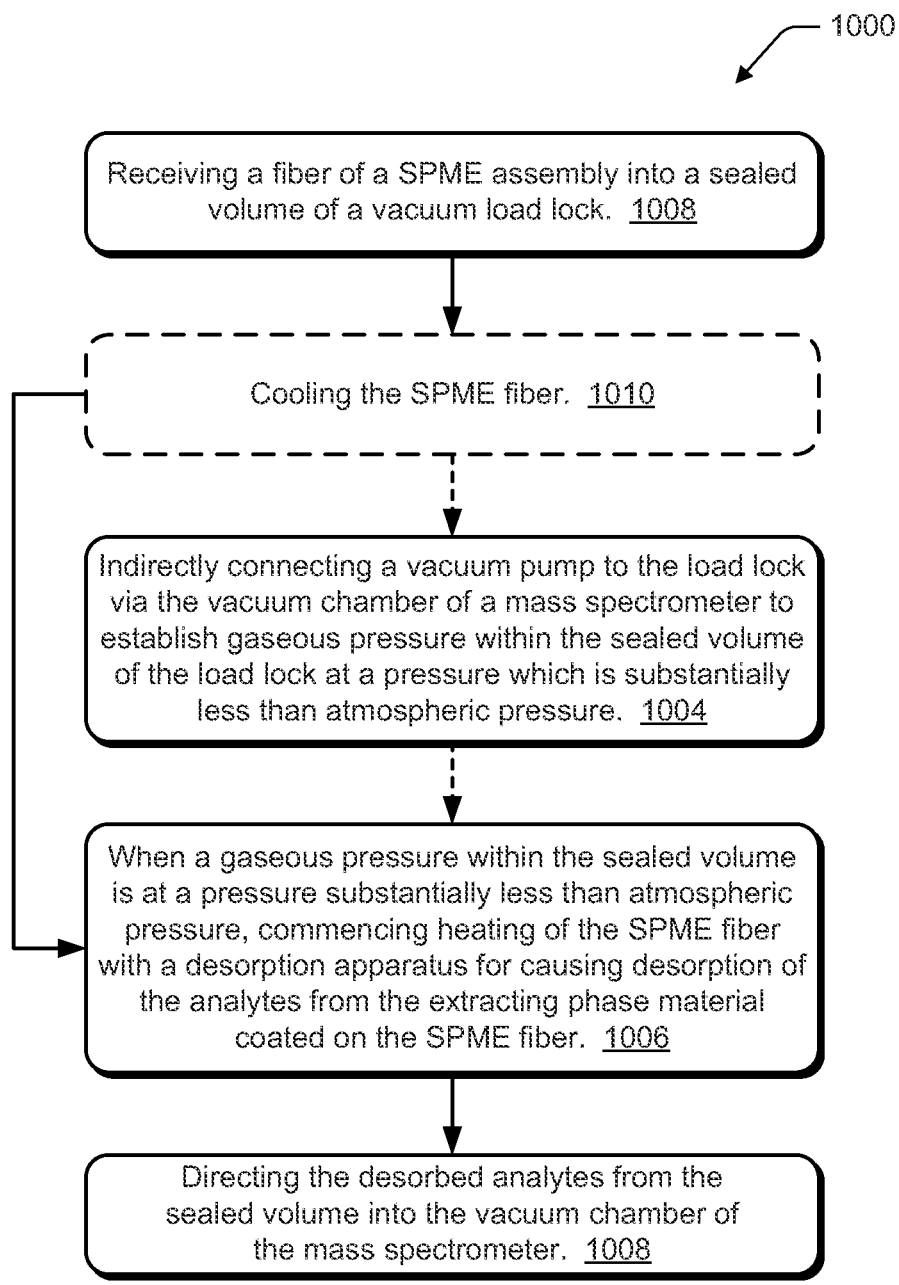

SOLID PHASE MICRO EXTRACTION (SPME) VACUUM INLET

BACKGROUND

Solid Phase Micro Extraction (SPME) is a sampling method in which analytes of interest are absorbed into or adsorbed onto a coating deposited on a fiber. The fiber is then transferred to an injection port of a separating analytical instrument, such as a gas chromatography (GC) system, where desorption of the analytes from the fiber occurs. The analytes travel through a capillary column of the GC system, which separates the analytes based upon their respective retention times. The separated analytes can then be delivered from the GC system column to a detector, for example a mass spectrometry (MS) system, e.g., a mass spectrometer. The MS system ionizes the analytes, separates the resulting ions according to their mass-to-charge ratios, detects the ions, generates signals based upon the detected ions, and then processes the resulting detected ion signals into mass spectra, from which the analytes can be identified.

Although use of a system that incorporates both GC and MS provides good selectivity, the time taken to run the analytes through the GC column can be approximately five (5) to ten (10) minutes, given typical GC column retention times. Further, GC can limit the library of analytes which can be detected by MS. For example, a GC-MS system does not allow for analysis of non-volatile analytes that will not pass through the GC column.

SUMMARY

A pressure vessel (e.g., vacuum load lock) configured for introducing a SPME sample into an analytical instrument system (e.g., mass spectrometer) is described. In implementations, the pressure vessel can include an enclosure forming a sealed volume, inlet and outlet ports connected to the enclosure, and a desorption component (e.g., heating element) located within the sealed volume. The desorption component is configured for heating a probe portion (e.g., SPME fiber) of a SPME assembly for causing desorption of analytes of the sample from an extracting phase material, which can be coated on the probe portion. The sealed volume of the pressure vessel is configured to receive the probe portion of the SPME assembly via the inlet port, and the inlet port is configured to form an airtight connection with the SPME assembly. The pressure vessel is configured to be connected to a vacuum pump for establishing a gaseous pressure within the sealed volume of the pressure vessel at a pressure substantially lower than atmospheric pressure. The outlet port of the pressure vessel is configured to be connected to a vacuum chamber of an analytical instrument system (e.g., mass spectrometer). When the gaseous pressure within the sealed volume of the pressure vessel is established at substantially lower than atmospheric pressure by the vacuum pump, heating of the probe portion commences for causing desorption of the analytes under near (e.g., partial) vacuum conditions. The desorbed analytes are then directed via the outlet port to the vacuum chamber. Thus, the pressure vessel (e.g., load lock) is configured for introducing the analytes of the SPME sample to the vacuum chamber of the analytical instrument system (e.g., mass spectrometer) at near vacuum pressure.

In other implementations, a mass spectrometer incorporating the pressure vessel (e.g., load lock), such as the pressure vessel described above, is described.

In further implementations, a method for introducing an analyte of a SPME sample into an analytical instrument system (e.g., mass spectrometer) is described. A probe portion of a SPME assembly is received into a sealed volume of a pressure vessel (e.g., vacuum load lock). The probe portion is coated with an extracting phase material, where the analyte is adsorbed onto and/or absorbed into the extracting phase material. When a gaseous pressure within the sealed volume is at a pressure substantially less than atmospheric pressure, heating of the probe portion is commenced using a desorption component located within the sealed volume. The desorption component is configured to cause desorption of the analyte from the extracting phase material. The desorbed analyte is directed from the sealed volume into a vacuum chamber of the analytical instrument system connected to the pressure vessel.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The detailed description is described with reference to the accompanying figures. In the figures, the left-most digit(s) of a reference number identify the figure in which the reference number first appears. The use of the same reference number in different instances in the description and the figures may indicate similar or identical items.

FIGS. 2A and 2B are partial cross-sectional elevation views illustrating a sample introduction system configured for implementation in, for example, the sample analysis system shown in FIG. 1A in accordance with example implementations of the present disclosure.

FIGS. 3A and 3B are partial cross-sectional elevation views illustrating a sample introduction system configured for implementation in, for example, the sample analysis system shown in FIG. 1B in accordance with example implementations of the present disclosure.

FIGS. 5A and 5B are cross-sectional views of a SPME assembly configured for implementation in, for example, the sample introduction systems shown in FIGS. 2A, 2B, 3A and 3B in accordance with example implementations of the present disclosure.

FIGS. 6A and 6B are cross-sectional views of a SPME assembly configured for implementation in, for example, the sample introduction systems shown in FIGS. 2A, 2B, 3A and 3B in accordance with example implementations of the present disclosure.

FIG. 10 is a flow diagram illustrating a method for sample introduction using, for example, the sample analysis system illustrated in FIG. 1B, in accordance with example implementations of the present disclosure.

DETAILED DESCRIPTION

Figure 1A:
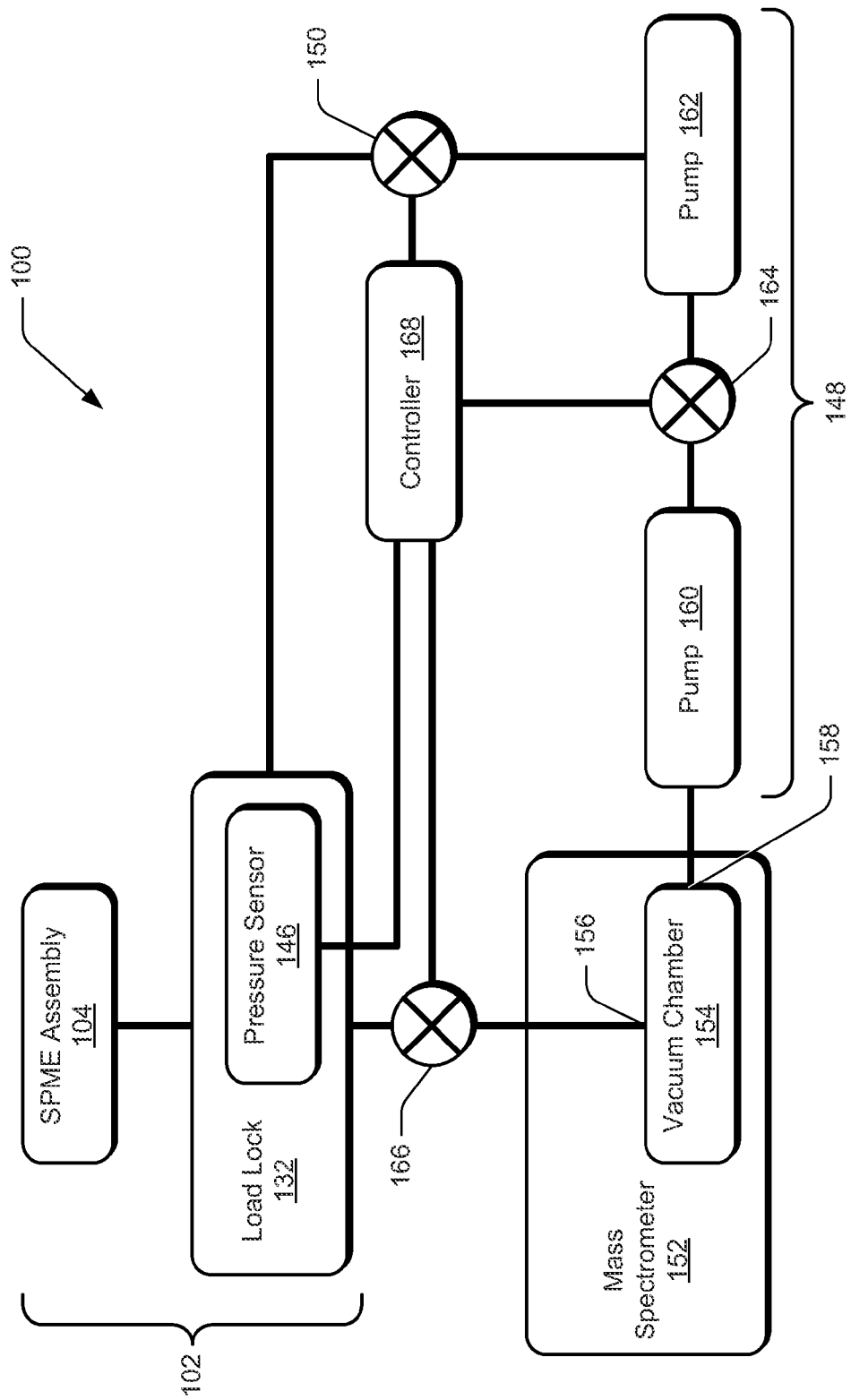
FIGS. 1A and 1B are diagrammatic illustration of sample analysis systems in accordance with example implementations of the present disclosure.

FIG. 1A is an illustration of a sample analysis system 100. The sample analysis system 100 includes a sample introduction system 102. The sample introduction system 102 can include, but is not necessarily limited to: a Solid Phase Micro Extraction (SPME) assembly 104. In implementations, the SPME assembly 104, examples of which are shown in FIGS. 4, 5A, 5B, 6A, 6B, 7A, 7B, 8A, and 8B, can be configured as a syringe-like device. For example, the SPME assembly 104 can include a housing 106 configured as a cylindrical tube or barrel forming a channel 108 which extends from a first end 110 of the housing 106 to a second end 112 of the housing 106. However, a cylindrical-shaped housing is provided by way of example only and is not meant to be restrictive of the present disclosure. Thus, other housing shapes may be used.

The SPME assembly 104 can include a needle 114 which is connected to the housing 106. The needle 114 can form a passage 116 which extends from a first end 118 of the needle 114 to a second end 120 of the needle 114. The first end 118 of the needle 114 can be connected to the second end 112 of the housing 106. The housing 106 can be connected to the needle 114 such that the channel 108 formed by the housing 106 is axially co-aligned with the passage 116 formed by the needle 114. The SPME assembly 104 can also include a plunger 122 which is slidably disposed within the channel 108 formed by the housing 106. The plunger 122 and the channel 108 may be sized so that the plunger 122, which is slidably disposed within the channel 108, fits snugly within the channel 108. Still further, the SPME assembly 104 can include a probe portion 124 connected to the plunger 122.

The plunger 122 can be moved in a first direction for causing the probe portion 124 to be directed into a first position (as shown in FIGS. 5A, 6A, 7A, and 8A). The plunger 112 can also be moved in a second direction for causing the probe portion 124 to be directed into a second position (as shown in FIGS. 5B, 6B, 7B, and 8B). When the probe portion 124 is in the first position, the plunger is located a first distance from the second end 112 of the housing 106 and the probe portion 124 is retracted into (e.g., is located at least substantially within and/or is located entirely within) the housing 106 and/or the needle 114. When the probe portion 124 is in the second position, the plunger 122 is located a second distance from the second end 112 of the housing 106, the second distance being less than the first distance, and the probe portion 124 protrudes from (e.g., beyond, outside of) the second end 120 of the needle 114. The SPME assembly 104 can be configured for causing the probe portion 124 to be biased towards the first position, such as via a spring-bias mechanism, or the like.

The plunger 122 can be configured for being manually actuatable and/or actuatable via an automated system for causing the probe portion 124 to be selectively moved into the first position and/or the second position. The plunger 122 can be configured to extend from (e.g., beyond, outside of) the first end 110 of the housing 106 for being accessible for actuation. The diameter of the passage 116 formed by the needle 114 can be less than the diameter of the channel 108 formed by the housing 106. The diameter of the passage 116 formed by the needle 114 can also be configured (e.g., sized) for preventing the plunger 122 from entering into the passage 116, thereby providing a stop mechanism for the downward movement of the plunger 122. A sealing device 126 can be located within the housing 106 and can be configured between the plunger 122 and the housing 106 of the SPME assembly 104 for forming an airtight or substantially airtight (e.g., vacuum tight) seal between the plunger 122 and the housing 106 (as shown in FIGS. 5A, 5B, 6A, and 6B). For example, the sealing device 126 can include one or more Teflon®-coated O-rings which are positioned between the plunger 122 and the housing 106. The sealing device 126 can be connected to and can move with the plunger 122 (as shown in FIGS. 5A and 5B), or the sealing device 126 can be connected to the housing 106 (as shown in FIGS. 6A and 6B).

Figure 7A:
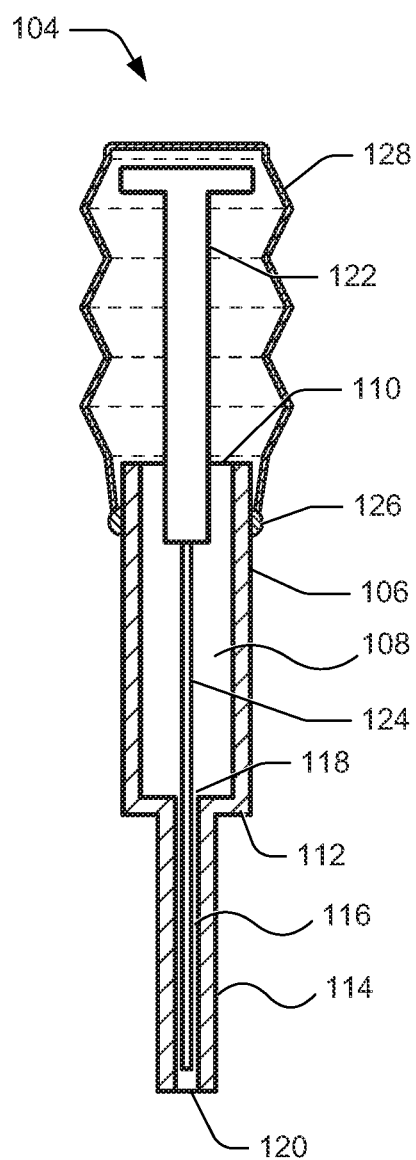
FIGS. 7A and 7B are cross-sectional views of a SPME assembly configured for implementation in, for example, the sample introduction systems shown in FIGS. 2A, 2B, 3A and 3B in accordance with example implementations of the present disclosure.
Figure 7B:
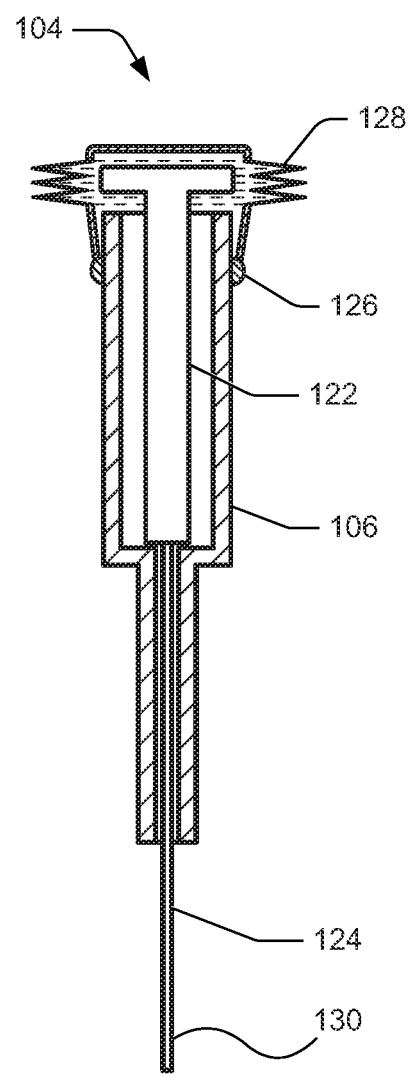
Figure 8A:
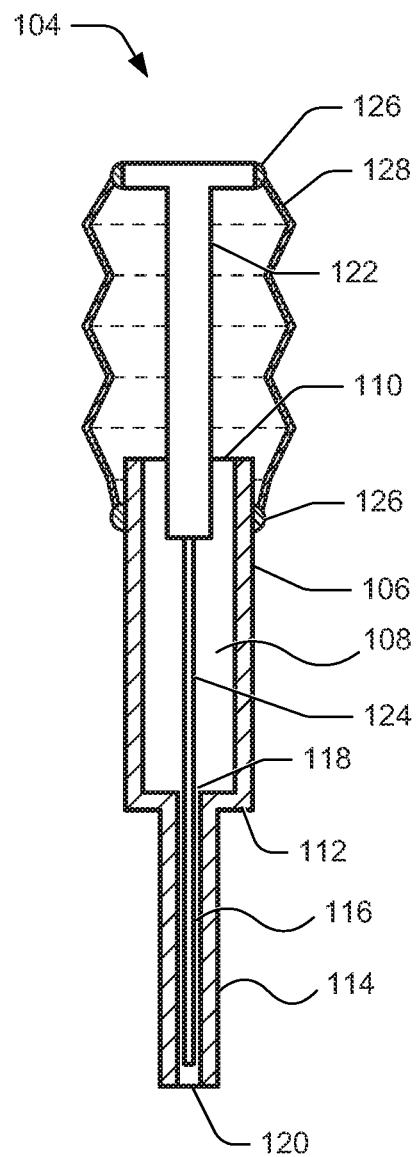
FIGS. 8A and 8B are cross-sectional views of a SPME assembly configured for implementation in, for example, the sample introduction systems shown in FIGS. 2A, 2B, 3A and 3B in accordance with example implementations of the present disclosure.
Figure 8B:
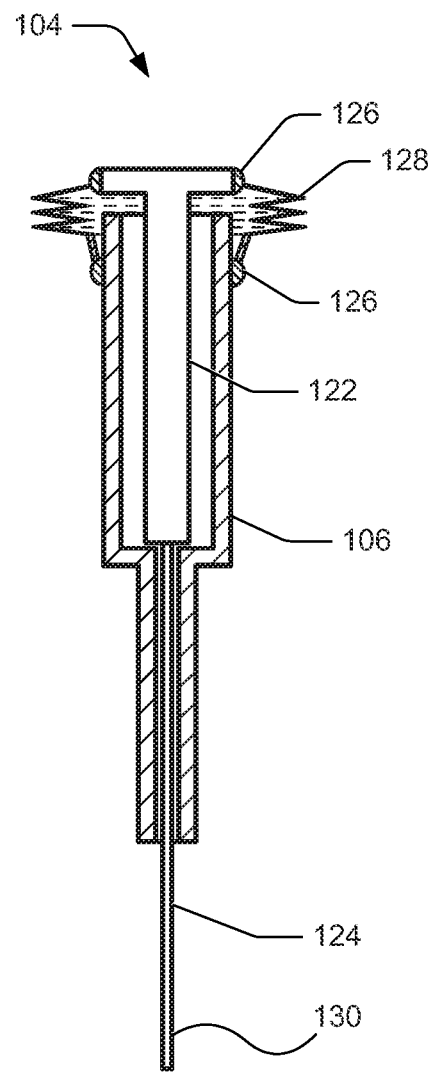

Additionally, an end seal device 128 can be configured to form a sealed (e.g., airtight, substantially airtight, vacuum tight) enclosure over the plunger 122 and the first end 110 of the housing 106 (as shown in FIGS. 6A, 6B, 7A and 7B). For example, the end seal device 128 can be a flexible structure, such as a bellows, and so forth, which can be configured for expansion (as shown in FIGS. 7A and 8A) and contraction (as shown in FIGS. 7B and 8B) to provide clearance for and/or to facilitate corresponding movement of the plunger 122. The end seal device 128 can be formed or molded over the plunger 122 and sealed to the housing 106 (as shown in FIGS. 7A and 7B), or the end seal device 128 can be sealed (e.g., molded) to both the housing 106 and the plunger 122 (as shown in FIGS. 8A and 8B).

In implementations, the probe portion 124 of the SPME assembly 104 can include, but is not necessarily limited to: a fiber, a roller and so forth. For example, the probe portion 124 can be a fiber with a diameter ranging from at least approximately ten micrometers (10 μm) to at least approximately one thousand micrometers (1,000 μm). Examples of roller or roller-type probes that can be used are disclosed in Soini, et al. 2006. "In Situ Surface Sampling of Biological Objects and Preconcentration of Their Volatiles for Chromatographic Analysis". *Analytical Chemistry* 78 (20) (October): 7161-7168, which is herein incorporated by reference. The probe portion 124 can be formed of a material such as a metal or a metal alloy. The probe portion 124 can be coated with an extracting phase material 130, such as a liquid (e.g., polymer) or a solid (e.g., sorbent), the extracting phase material configured for extracting analytes (e.g., volatile analytes and/or non-volatile analytes) from different types of media (e.g., liquid phase and/or gas phase). Examples of extracting phase material which can be used include, but are not necessarily limited to: Polydimethysiloxane (PDMS); polyacrylate (PA); Polydimethylsiloxane/Divinylbenzene (PDMS/DVB); Carboxen/Polydimethylsiloxane (CAR/PDMS); Carbowax/Divinylbenzene (CW/DVB); Carbowax/Templated Resin (CW/TPR); Divinylbenzene/Carboxen/Polydimethylsiloxane (DVB/CAR/PDMS); Polypyrrole; mesoporous silica; molecularly-imprinted polymers; ionic imprinted polymers; immunosorbents; and sol-gel coatings. The probe portion (e.g., SPME fiber), when coated with the extracting phase material 130, acts as an efficient pre-concentrator of analytes.

As mentioned above, the SPME assembly 104 can be utilized to extract volatile analytes and/or non-volatile analytes (e.g., organics, chemicals, and so forth) from a gas or a liquid. For example, when the probe portion 124 is in the second position (e.g., as shown in FIG. 4B), such that the probe portion 124 protrudes from the second end 120 of the needle 114, the probe portion 124 may be waved through a gas and/or dipped in a liquid, so that analytes (e.g., sample) can be absorbed into or adsorbed onto the extracting phase material 130 deposited on the probe portion 124. In instances where the probe portion 124 is configured as a roller, the probe portion 124 can be configured for extracting analytes (e.g., obtaining a sample) by rolling across a surface. After the analytes have been extracted by the extracting phase material 130 on the probe portion 124, the probe portion 124 can be placed into the first position (as shown in FIG. 4A), such that the probe portion 124 is refracted into the housing 106 and/or the needle 114 (e.g., for protecting the probe portion 124 from mechanical damage, contamination, and so forth).

The sample introduction system 102 can further include a pressure vessel 132 (e.g., as shown in FIG. 1A). For example, the pressure vessel 132 can be a load lock, such as a vacuum load lock. The pressure vessel 132 can be connected to the SPME assembly 104. The pressure vessel 132 can include an inlet port 134, a first outlet port 136, and a second outlet port 138 (as shown in FIGS. 2A and 2B). As shown in FIGS. 2A and 2B, the needle 114 of the SPME assembly 104 can be connected to the inlet port 134 of the pressure vessel 132. The connection between the SPME assembly 104 and the inlet port 134 can be configured for promoting ease of connection and removal of the SPME assembly 104 from the pressure vessel 132. In some instances, the connection between the SPME assembly 104 and the inlet port 134 of the pressure vessel 132 can be a sealed connection. For example, a sealing mechanism 140 (e.g., septum), such as one or more O-rings, can be utilized for sealing the connection between the SPME assembly 104 and the inlet port 134. However, O-rings are provided by way of example only and are not meant to be restrictive of the present disclosure. Thus, other various sealing mechanisms may also be used to seal the connection between the SPME assembly 104 and the inlet port 134. In implementations, the sealed connection between the SPME assembly 104 and the inlet port 134 can be airtight or substantially airtight (e.g., vacuum tight). For example, the connection between the SPME assembly 104 and the inlet port 134 of the pressure vessel 132 can be a screw-down connection with one or more O-rings sealing the connection. Further, in some instances, the connection between the SPME assembly 104 and the inlet port 134 can be a flexible connection.

The pressure vessel 132 can include a desorption component 142, which can be located within a sealed volume 144 formed by the pressure vessel 132. The desorption component 142 can be configured for receiving the probe portion 124 of the SPME assembly 104 after the probe portion 124 is introduced into the sealed volume 144 via the inlet port 134 of the pressure vessel 132. The pressure vessel 132 can be configured for receiving only the probe portion 124 into the sealed volume 144 via the inlet port 134, and/or the pressure vessel 132 can be configured for receiving both the probe portion 124 and at least a portion of the needle 114 into the sealed volume 144 via the inlet port 134. The probe portion 124 can be received within the desorption component 142 upon introduction into the sealed volume 144 of the pressure vessel (e.g., a single stage introduction), or the probe portion 124 can be directed into the sealed volume 144 and then moved into the second position (e.g., as shown in FIG. 5B) so that as the probe portion 124 is moved into the second position, it is introduced into the desorption component 142 (e.g., for two-stage introduction). For example, in the two-stage introduction, the desorption component 142 (e.g., heating element) can be configured such that it is always on (e.g., in heating mode, activated). The desorption component 142 can be configured to cause desorption of one or more analytes from the extracting phase material 130 coated on the probe portion 124.

The desorption component 142 can be a heating element which is configured for operating in a first mode (e.g., a heating mode) in which the desorption component 142 heats the probe portion 124 and the extracting phase material 130 to cause desorption of the analytes from the extracting phase material 130. The desorption component 142 can also comprise a cooling element configured for operating in a second mode (e.g., a cooling mode), in which the desorption component 142 cools the probe portion 124 and the extracting phase material 130. In some instances, the desorption component 142 can be a metal structure that is sized for receiving (e.g., fitting around) at least a portion of the probe portion 124. The desorption component 142 can be positioned proximal to the first outlet port 136 of the pressure vessel 132. The desorption component 142 can be configured for being powered on and off.

The desorption component 142 can be configured for operating in the heating mode (e.g., the heating mode of the desorption component 142 can be activated or powered on) upon a triggering event such as, but not necessarily limited to: pressure within the sealed volume 144 of the pressure vessel 132 reaching or decreasing below a threshold pressure. Further, the desorption component 142 can be configured to have an adjustable operating temperature. The desorption component 142 can be configured to be selectively switch between a heating mode and a cooling mode. The pressure vessel 132 can include a pressure sensor 146. The pressure sensor 146 can be configured for sensing and/or monitoring a pressure within the sealed volume 144 of the pressure vessel 132.

The pressure sensor 146 can be connected to a controller 168. The desorption component 142 can be connected to the controller 168. The controller 168 can be configured for controlling the above-described functionality of the desorption component 142. For example, the controller 168 can be configured for controlling the functionality of the desorption component 142 based upon signals the controller 168 receives from the pressure sensor 146. When the SPME assembly 104 is connected to the pressure vessel 132, the desorption component 142, the inlet port 134, the needle 114 and/or the probe portion 124 can be axially co-aligned to promote ease of introduction of the probe portion 124 into the inlet port 134 and the desorption component 142.

As shown in FIG. 1A, the sample analysis system 100 can further include a pump system (e.g., a vacuum pump system) 148 configured for connecting to the pressure vessel 132. For example, the pump system 148 can be connected to the second outlet port 138 of the pressure vessel 132. The pump system 148 can be configured to remove gas molecules via the second outlet port 138 from the sealed volume 144 formed by the pressure vessel 132 to create a partial vacuum within the sealed volume 144. For instance, the pump system 148 can be configured to cause the sealed volume 144 of the pressure vessel to have a gaseous pressure of substantially less than atmospheric pressure. In some instances, the pump system 148 can be configured to pump the sealed volume 144 down to a pressure which is substantially a vacuum pressure or near a vacuum pressure (e.g., less than at least approximately one hundred millitorr (mTorr)). A valve 150 can be positioned between the pump system 148 and the sealed volume 144 to allow the sealed volume 144 of the pressure vessel 132 to be selectively connected to or disconnected from the pump system 148. For example, valve 150 can be located proximate to and/or within the second outlet port 138 (e.g., as shown in FIGS. 2A and 2B). The valve 150 can be manually actuatable and/or actuatable via an automated system for allowing the sealed volume 144 of the pressure vessel 132 to be selectively connected to or disconnected from the pump system 148.

As mentioned above, the desorption component 142 can utilize heating to cause desorption of the analytes from the extracting phase material 130. The extracting phase material 130 can be selected such that, when exposed to environments having a gaseous pressure which is substantially less than atmospheric pressure, the analytes maintain adherence to (e.g., do not desorb from) the extracting phase material 130 until they are heated by desorption component 142.

Figure 1B:
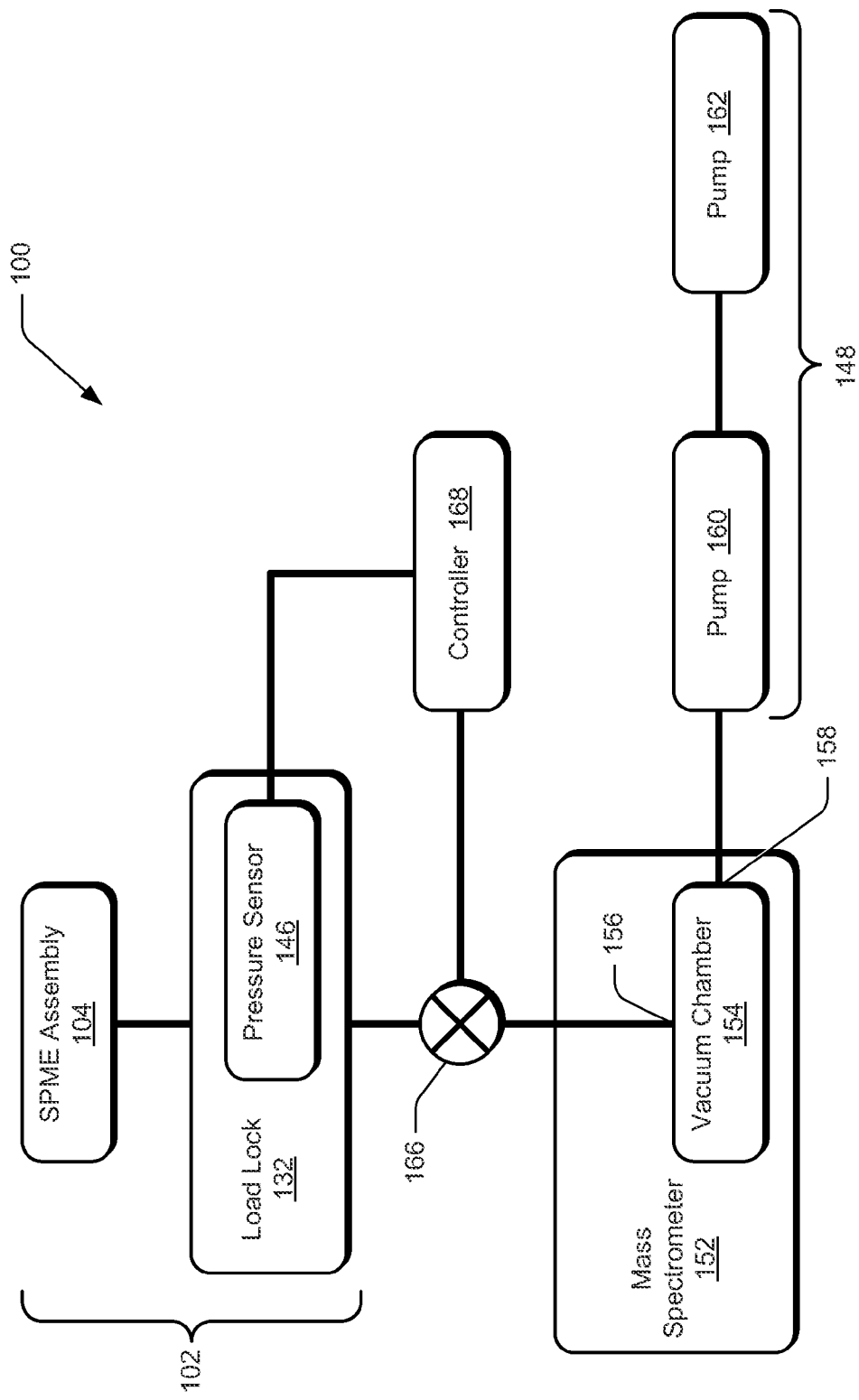
Figure 4:
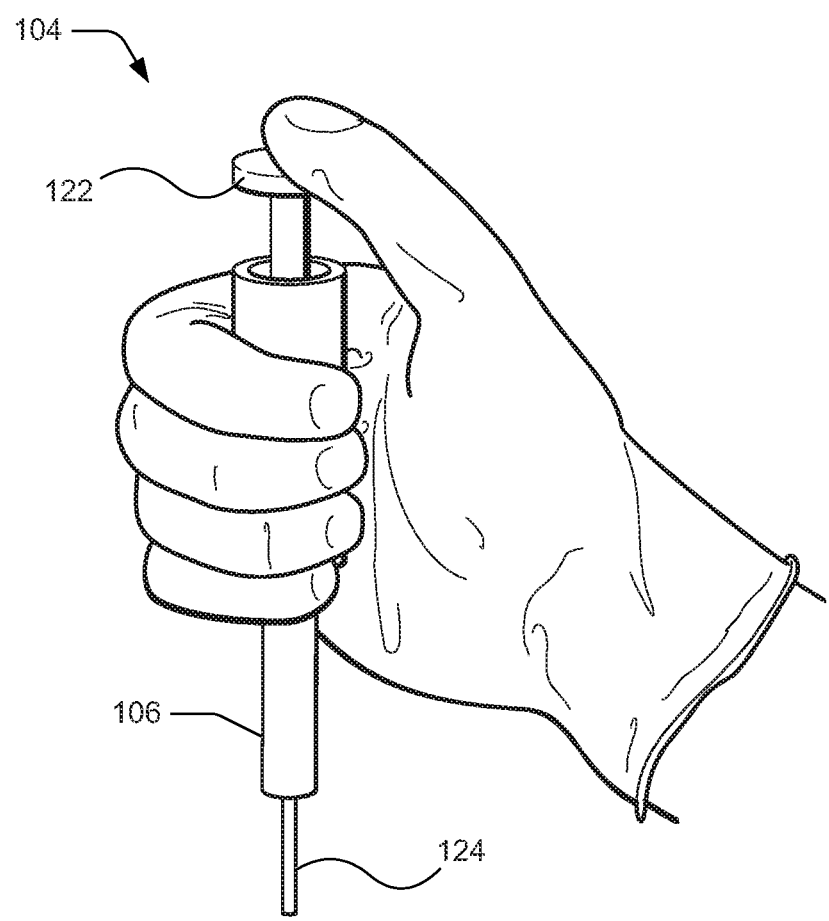
FIG. 4 is an isometric view illustrating the use of a SPME assembly configured for implementation in the sample introduction systems shown in FIGS. 2A, 2B, 3A and 3B.

The sample analysis system 100 can include an analytical instrument system 152 configured to connect to the pressure vessel 132 (e.g., as shown in FIG. 1A). The analytical instrument system 152 can be any system (e.g., a mass spectrometer (MS), a tandem mass spectrometry (MS-MS) system, and so forth) configured for operating in an environment having a gaseous pressure of substantially less than atmospheric pressure (e.g., a partial vacuum). As shown in FIGS. 1A and 1B, the analytical instrument system 152 can be a mass spectrometer. The analytical instrument system 152 can include a vacuum chamber 154 which includes an inlet 156 and an outlet 158. The inlet 156 of the vacuum chamber 154 is configured to connect to the second outlet port 138 of the pressure vessel 132. For example, the pressure vessel 132 can be integral with (e.g., included as part of) the analytical instrument system 152, and/or the pressure vessel 132 can be configured for being removably connected to the analytical instrument system 152. The inlet 156 of the vacuum chamber 154 can be configured to receive the desorbed analytes as described above via the second outlet port 138 of the pressure vessel 132. The outlet 158 of the vacuum chamber 154 can be configured to connect to the pump system 148. The pump system 148 can be configured for removing gas molecules from the vacuum chamber 154 via the outlet 158 to create a partial vacuum within the vacuum chamber 154.

The analytical instrument system 152 can also include analytical instrumentation located within the vacuum chamber 154 for analyzing the desorbed analytes. For example, in implementations where the analytical instrument system 152 is a mass spectrometer, the analytical instrumentation located within the vacuum chamber 154 can include, but is not necessarily limited to: an ion source, where the ion source is configured for ionizing (e.g., generating ions from) the desorbed analytes; a mass analyzer (e.g., mass filter, ion trap) connected to the ion source, where the mass analyzer is configured for separating the generated ions based upon their mass-to-charge ratios; a detector connected to a mass analyzer, where the detector is configured for detecting the separated ions and generating signals (e.g., data) based upon the detected ions, and so forth. The data can be processed by a computing system, which may be included with or connected to the analytical instrument system 152, for calculating the abundances of each ion present among the detected ions and/or for generating an output (e.g., mass spectra) based upon comparing the processed signals to data stored in a database of the computing system. In further embodiments, the ion source can be located within the pressure vessel (e.g., load lock) 132 and the generated ions can be moved towards the mass spectrometer using electric fields.

The pump system 148 can include a plurality of pumps including a turbomolecular pump 160 and/or a roughing pump 162. The turbomolecular pump 160 can be connected to the roughing pump 162. A valve 164 can be configured between the turbomolecular pump 160 and the roughing pump 162 for allowing the turbomolecular pump 160 to be selectively connected to or disconnected from the roughing pump 162 and/or for allowing the pressure vessel 132 to be selectively connected to or disconnected from the turbomolecular pump 160 and/or the roughing pump 162. The valve 164 can be manually actuatable and/or actuatable via an automated system for allowing the turbomolecular pump 160 to be selectively connected to or disconnected from the roughing pump 162 and/or for allowing the pressure vessel 132 to be selectively connected to or disconnected from the turbomolecular pump 160 and/or the roughing pump 162. Further, the turbomolecular pump 160 can be integral with the vacuum chamber 154 of the analytical instrument system 152.

The sample analysis system 100 can include a valve 166 configured between the pressure vessel 132 and the analytical instrument system 152 for allowing the pressure vessel to be selectively connected to or disconnected from the vacuum chamber 154 of the analytical instrument system 152. For example, valve 166 can be located proximate to and/or within the first outlet port 136 of the pressure vessel 132 (as shown in FIGS. 2A and 2B). The valve 166 can be manually actuatable and/or actuatable via an automated system for allowing the pressure vessel to be selectively connected to or disconnected from the vacuum chamber 154. As mentioned above, the sample analysis system 100 can include controller 168. The controller 168 can be connected to the pressure sensor 146 of the pressure vessel 132 and valve 150. For example, the controller 168, pressure sensor 146 and valve 150 can form a feedback circuit in which the controller 168, based upon signals received from the pressure sensor 146, can selectively open or close valve 150 to connect the pressure vessel 132 to or disconnect the pressure vessel 132 from the vacuum system 148. In embodiments, when a pump down time of the pressure vessel 132 is accurately known, the pressure vessel 132 can be configured for being connected to the vacuum system 148 based upon an amount of time elapsed since commencement of pump down of the pressure vessel 132.

The controller 168 can be connected to valve 166 and can selectively open or close valve 166 to connect the pressure vessel 132 to or disconnect the pressure vessel 132 from the vacuum chamber 154 based upon signals received from the pressure sensor 146. Further, the controller 168 can be connected to valve 164 and can selectively open or close valve 164 to connect the pressure vessel 132 to or disconnect the pressure vessel 132 from the turbomolecular pump 160 and/or the roughing pump 162 and/or connect the turbomolecular pump 160 to the roughing pump 162. The controller 168 can be connected to the desorption component 142 for powering the desorption component on and off and/or for controlling an operating temperature of the desorption component 142.

FIG. 1B is an illustration of another implementation of the sample analysis system 100. The sample analysis system 100 shown in FIG. 1B can include sample introduction system 102, including SPME assembly 104 and pressure vessel 132, where the pressure vessel 132 is configured for being connected to the SPME assembly 104 via sealing mechanism 140, as described above. In the implementation shown in FIG. 1B, the pressure vessel 132 can form sealed volume 144 and can include inlet port 134, outlet port 136, desorption component 142, and pressure sensor 146, as described above. The sample analysis system 100 shown in FIG. 1B can include controller 168, the controller 168 being connected to the pressure sensor 146 and the desorption component 142 of the pressure vessel 132, as described above.

The sample analysis system 100 shown in FIG. 1B can include analytical instrument system 152 (e.g., a mass spectrometer), the analytical instrument system 152 configured for being connected to the pressure vessel 132, as described above. The sample analysis system 100 shown in FIG. 1B can include a pump system (e.g., vacuum pump system) 148, as described above. However, the pump system 148 illustrated in FIG. 1B does not include valve 164 between the turbomolecular pump 160 and the roughing pump 162. The pump system 148 can be configured for being connected to the analytical instrument system 152, as described above. In the implementation shown in FIG. 1B, the pump system 148 is indirectly connected to the pressure vessel 132 via the analytical instrument system 152. Thus, in the implementation shown in FIG. 1B, because the pressure vessel 132 is not directly connected to the pump system 148, the pressure vessel 132 does not include second outlet port 138 for connecting the pressure vessel 132 to the pump system 148.

The sample analysis system 100 shown in FIG. 1B can include valve 166 configured between the pressure vessel 132 and the analytical instrument system 152. As described above, valve 166 can be configured for allowing the pressure vessel 132 to be selectively connected to or disconnected from the vacuum chamber 154 of the analytical instrument system 152. In the implementation shown in FIG. 1B, the configuration of valve 166 can allow the pressure vessel 132 to be indirectly connected to the pump system 148 via the vacuum chamber 154. For example, controller 168 can be connected to valve 166 and can selectively open or close valve 166 to connect the pressure vessel 132 to or disconnect the pressure vessel 132 from the vacuum chamber 154. In embodiments, valve 166 can be a continuous valve which can be opened relatively slowly, rather than being an on/off valve, in order to minimize pressure pulse and maximize vacuum chamber pressure during pump down.

In the sample analysis system 100 shown in FIG. 1B, controller 168 can be connected to the pressure sensor 146 and desorption component 142 in a feedback loop. The controller 168 can be configured for selectively powering the desorption component 142 on and off and/or for selectively controlling an operating temperature of the desorption component 142 based upon signals received from the pressure sensor 146.

The sample analysis system implementations described herein can be implemented as stand-alone system, or can be incorporated within a larger system, such as a portable chemical detection device. For example, the portable chemical detection device may be configured with a computer system including: a processor; memory; a display; a user interface; hardware; software modules; and firmware.

Example Procedures

The following discussion describes procedures that may be implemented using the above-described implementations of the sample analysis system 100. The procedures are shown as a set of blocks that specify operations performed by one or more devices and are not necessarily limited to the order shown for performing the operations by the respective blocks. In portions of the following discussion, reference will be made to the sample analysis system implementations of FIGS. 1A and 1B.

Figure 9:
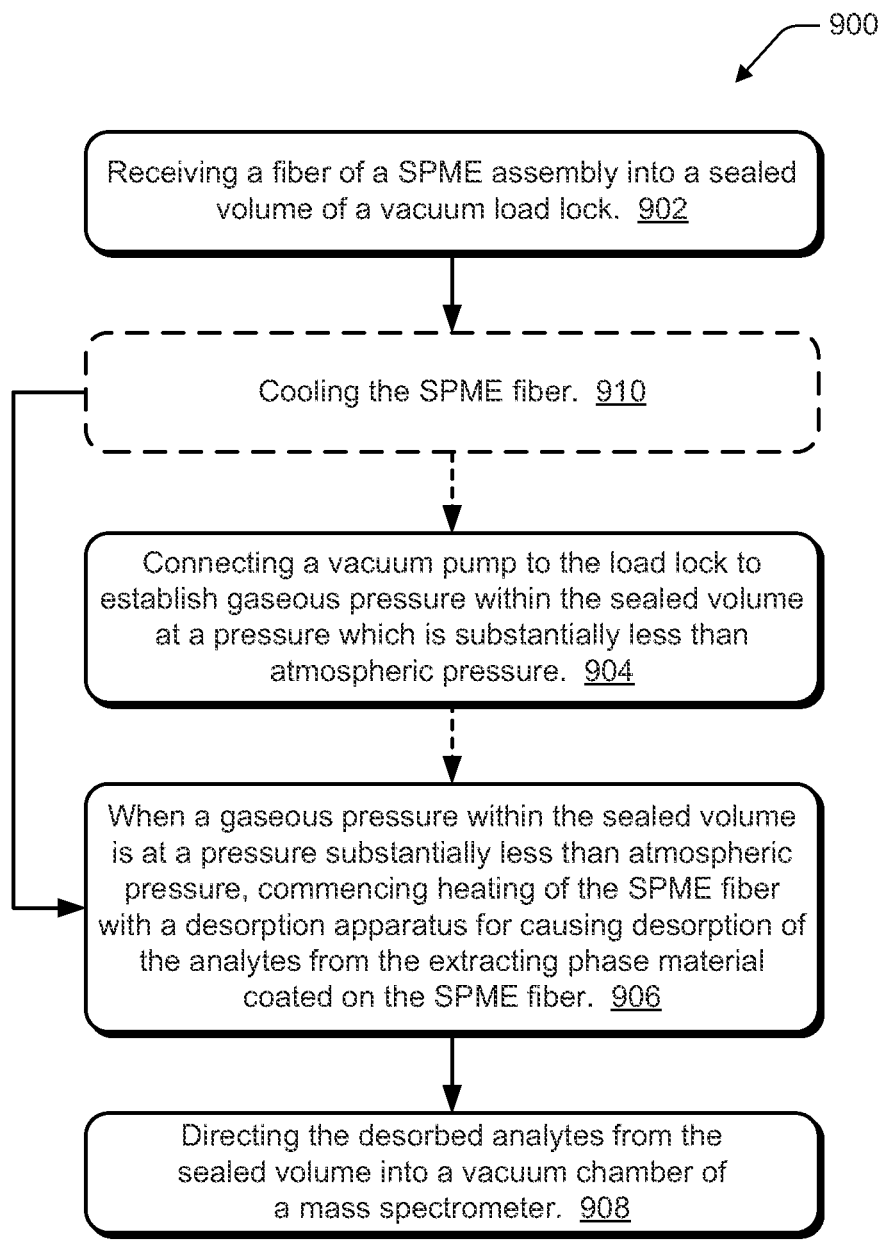
FIG. 9 is a flow diagram illustrating a method for sample introduction using, for example, the sample analysis system illustrated in FIG. 1A, in accordance with example implementations of the present disclosure.

FIG. 9 depicts a procedure 900 in an example implementation for introducing a sample (e.g., one or more analytes) into the analytical instrument system (e.g., a mass spectrometer) of the sample analysis system implementation shown in FIG. 1A. In implementations, the procedure 900 may be performed under automated (e.g., computer) control.

In implementations, the procedure 900 can include receiving a probe portion (e.g., fiber) of a solid phase micro extraction (SPME) assembly into a sealed volume of a pressure vessel (e.g., vacuum load lock) (block 902). For example, the probe portion (e.g., SPME fiber) 124 can be received into the sealed volume 144 of the pressure vessel 132 via an inlet port 134. The probe portion 124 can be coated with extracting phase material 130. The analytes can be adsorbed onto and/or absorbed into the extracting phase material 130. During introduction of the probe portion 124 into the pressure vessel 132, valve 166 and valve 150, which are configured for selectively connecting the sealed volume 144 of the pressure vessel 132 to the vacuum chamber 154 of the analytical instrument system (e.g., mass spectrometer) 152 and the pump system (e.g., vacuum pump(s)) 148 respectively, are both in a closed position.

In implementations, the procedure 900 can include connecting a pump system (e.g., one or more vacuum pumps) to the pressure vessel (e.g., load lock) to establish gaseous pressure within the sealed volume at a pressure which is substantially less than atmospheric pressure (block 904). This step can be referred to as the pump-down step (e.g., pump-down). In the implementation of the sample analysis system 100 shown in FIG. 1A, just prior to pump-down, valve 164 can be established in a closed position. When valves 164 and 166 are in the closed position prior to pump-down, valve 150 can then be established in an open position for connecting (e.g., allowing airflow between) the pump system 148 and the pressure vessel 132 to initiate pump-down. For instance, as shown in FIG. 1A, valve 150 can be opened to connect the pressure vessel (e.g., vacuum load lock) 132 to the roughing pump 162 of the vacuum pump system 148 to initiate pump-down. During pump-down, the pump system 148 reduces the gaseous pressure within the sealed volume 144 until the gaseous pressure within the sealed volume is substantially less than atmospheric pressure (e.g., less than 100 mTorr).

In implementations, the system 100 can be configured so that the time it takes to complete pump-down of the pressure vessel 132 (e.g., the time it takes to reduce the gaseous pressure within the sealed volume 144 of the pressure vessel (e.g., load lock) 132 to a desired pressure that is substantially less than atmospheric pressure (e.g. less than 100 mTorr)) can be less than ten seconds. For example, by configuring the pressure vessel 132 such that the size of the sealed volume (e.g., dead volume) 144 around the probe portion 124 (e.g., fiber) is minimized, pump-down time for the pressure vessel 132 can be likewise be minimized. Further, during or subsequent to pump-down of the pressure vessel 132, valve 164 can be established in an open position for connecting (e.g., allowing airflow between) the pump system 148 and the vacuum chamber 154 of the analytical instrument system (e.g., mass spectrometer) 152. For example, valve 164 can be opened to connect both the roughing pump 162 and the turbomolecular pump 160 to the vacuum chamber 154 for establishing the gaseous pressure within the vacuum chamber 154 at a pressure which is at or near vacuum (e.g., partial vacuum, substantially less than atmospheric pressure).

In implementations, when a gaseous pressure within the sealed volume is at a pressure substantially less than atmospheric pressure, the procedure 900 can include commencing heating of the probe portion with a desorption component for causing desorption of the analytes from the extracting phase material (block 906). The desorption component (e.g., heating element) 142 can be located within the sealed volume 144. For example, heating of the probe portion (e.g., fiber) 124 for causing desorption of the analytes can begin after the gaseous pressure with the sealed volume 144 of the pressure chamber 132 (e.g., load lock) is established at a pressure which is substantially below atmospheric pressure and is slightly above the gaseous pressure established in the vacuum chamber 154 of the analytical instrument system (e.g., mass spectrometer) 152. By waiting until the above-described pressure conditions are established within the sealed volume 144 to begin heating, analyte desorption from the probe portion 124 (e.g., SPME fiber) can be furnished under partial vacuum (e.g., near vacuum) conditions, rather than at atmospheric pressure. Further, after the above-described pressure conditions are established, and prior to beginning heating of the probe portion 124, valve 150 can be moved to a closed position and valve 166 can be moved to an open position for connecting (e.g., creating an airflow between) the sealed volume 144 of the pressure chamber 132 and the vacuum chamber 154 of the analytical instrument system (e.g., mass spectrometer) 152. This allows for the gaseous pressure within the pressure vessel (e.g., load lock) 132 to further approach (e.g., become equal to) the gaseous pressure within the vacuum chamber 154 of the analytical instrument system (e.g., mass spectrometer) 152.

As mentioned previously, the pressure vessel 132 can include pressure sensor 146 which can be connected to controller 168 and valve 166 to form a feedback circuit. The pressure sensor 146 can provide a signal to the controller 168 indicating that the desired pressure conditions within the sealed volume 144 of the pressure vessel 132 have been established, and based upon this signal, the controller 168 can open valve 166 to connect the sealed volume 144 and the vacuum chamber 154. The desorption component 142 can also be connected to controller 168 and pressure sensor 146 in a feedback circuit configuration. For example, the pressure sensor 146 can provide a signal to the controller 168 indicating that the desired pressure conditions within the sealed volume 144 of the pressure vessel 132 have been established, and based on this signal, the controller 168 can power on the desorption component 142 to commence heating of the probe portion 124.

In implementations, the procedure 900 can include directing the desorbed analytes from the sealed volume into a vacuum chamber of the analytical instrument system (block 908). The vacuum chamber 154 of the analytical instrument system (e.g., mass spectrometer) 152 is connected to the sealed volume 144 of the pressure vessel (e.g., load lock) 132. As mentioned above, just prior to opening valve 166, the gaseous pressure within the sealed volume 144 can be just slightly higher than the gaseous pressure within the vacuum chamber 154. This pressure differential can be achieved by configuring the pressure vessel 132 to have a slight pressure leak. Once valve 166 is opened and heating of the probe portion 124 begins, this pressure differential can facilitate the flow of desorbed analytes from the sealed volume 144 of the pressure vessel 132 into the vacuum chamber 154 of the analytical instrument system 152. Further, by having the desorption component 142 located in close proximity to outlet port 136 of the pressure vessel 132, efficiency of transfer of the desorbed analytes from the pressure vessel 132 to the analytical instrument system 152 is promoted. Still further, selection of the extracting phase material 130 can play a role in promoting efficient transfer of the desorbed analytes from the pressure vessel 132 to the analytical instrument 152. For example, selecting extracting phase material 130 from which desorption of analytes does not occur under the above-described pump-down conditions, but from which desorption of analytes does occur during heating of the probe portion 124 by the desorption component 142 can promote efficient transfer of desorbed analytes from the pressure vessel 132 to the analytical instrument 152.

In implementations, prior to connecting the pump system (e.g., vacuum pump(s)) to the pressure vessel (e.g., load lock), the procedure 900 can include cooling the probe portion (e.g., fiber) (block 910). For example, when the analytes which are adsorbed onto and/or absorbed into the extracting phase material 130 include high volatility analytes, there could be a risk of those analytes being desorbed (e.g., released) from the probe portion (e.g., SPME fiber) 124 prematurely, such as during pump-down of the pressure vessel 132 (e.g., during the process of reducing the pressure within the sealed volume of the load lock to near vacuum pressure by the vacuum pump(s)). Cooling the probe portion (e.g., SPME fiber) 124 prior to pump-down can counteract and/or prevent the possibility of analyte desorption prior to a desired pressure being established within the sealed volume 144 of the pressure vessel 132. The desorption component 142 can be configured with a cooling element (e.g., a fan) for cooling the probe portion 124.

FIG. 10 depicts a procedure 1000 in an example implementation for introducing a sample (e.g., one or more analytes) into the analytical instrument system (e.g., a mass spectrometer) of the sample analysis system implementation shown in FIG. 1B. In implementations, the procedure 1000 may be performed under automated (e.g., computer) control.

In implementations, the procedure 1000 can include receiving a probe portion (e.g., fiber) of a solid phase micro extraction (SPME) assembly into a sealed volume of a pressure vessel (e.g., vacuum load lock) (block 1002). For example, the probe portion (e.g., SPME fiber) 124 can be received into the sealed volume 144 of the pressure vessel 132 via an inlet port 134. The probe portion 124 can be coated with extracting phase material 130. The analytes can be adsorbed onto and/or absorbed into the extracting phase material 130. During introduction of the probe portion 124 into the pressure vessel 132, valve 166, which is configured for selectively connecting (e.g., allowing airflow between) the sealed volume 144 and the vacuum chamber 154, can be in a closed position. In the sample analysis system implementation shown in FIG. 1B, the vacuum chamber 154 of the analytical instrument system (e.g., mass spectrometer) 152 can be connected to pump system (e.g., one or more vacuum pumps) 148, such that an airflow is established between the pump system 148 and the vacuum chamber 154. For example, the vacuum chamber 154 can be connected to both a roughing pump 162 and turbomolecular pump 160 for establishing the gaseous pressure within the vacuum chamber 154 at a pressure which is at or near vacuum (e.g., partial vacuum, substantially less than atmospheric pressure).

In implementations, the procedure 1000 can include indirectly connecting the pump system (e.g., one or more vacuum pumps) to the pressure vessel (e.g., load lock) via the vacuum chamber of the analytical instrument system to establish gaseous pressure within the sealed volume at a pressure which is substantially less than atmospheric pressure (block 1004). This step can be referred to as the pump-down step (e.g., pump-down). In the implementation of the sample analysis system 100 shown in FIG. 1B, to commence pump-down, valve 166 can be established in an open position for indirectly connecting (e.g., allowing airflow between) the pump system 148 and the pressure vessel 132, via the vacuum chamber 154, to initiate pump-down. During pump-down, the pump system 148 reduces the gaseous pressure within the sealed volume 144 until the gaseous pressure within the sealed volume is substantially less than atmospheric pressure (e.g., less than 100 mTorr). The system 100 can be configured so that the time it takes to complete pump-down of the pressure vessel 132 (e.g., the time it takes to reduce the gaseous pressure within the sealed volume 144 of the pressure vessel (e.g., load lock) 132 to a desired pressure that is substantially less than atmospheric pressure (e.g. less than 100 mTorr)) can be less than ten seconds. For example, by configuring the pressure vessel 132 such that the size of the sealed volume (e.g., dead volume) 144 around the probe portion 124 (e.g., fiber) is minimized, pump-down time for the pressure vessel 132 can be likewise be minimized.

In implementations, when a gaseous pressure within the sealed volume is at a pressure substantially less than atmospheric pressure, the procedure 1000 can include commencing heating of the probe portion with a desorption component for causing desorption of the analytes from the extracting phase material (block 1006). The desorption component (e.g., heating element) 142 can be located within the sealed volume 144. For example, heating of the probe portion (e.g., fiber) 124 for causing desorption of the analytes can begin after the gaseous pressure with the sealed volume 144 of the pressure chamber 132 (e.g., load lock) is established at a pressure which is substantially below atmospheric pressure and is slightly above the gaseous pressure established in the vacuum chamber 154 of the analytical instrument system (e.g., mass spectrometer) 152. This pressure differential can be achieved by keeping a slight leak in the pressure vessel 132. Once valve 166 is opened, and heating of the probe portion 124 begins, this pressure differential can facilitate the flow of desorbed analytes from the sealed volume 144 of the pressure vessel 132 into the vacuum chamber 154 of the analytical instrument system 152. By waiting until the above-described pressure conditions are established within the sealed volume 144 to begin heating, analyte desorption from the probe portion 124 (e.g., SPME fiber) is allowed to happen under partial vacuum (e.g., near vacuum) conditions, rather than at atmospheric pressure. As mentioned previously, the pressure vessel 132 can include pressure sensor 146 which can be connected to controller 168. In implementations, the desorption component 142 can be connected to controller 168 and pressure sensor 146 in a feedback circuit configuration. For example, the pressure sensor 146 can provide a signal to the controller 168 indicating that the desired pressure conditions within the sealed volume 144 of the pressure vessel 132 have been established, and based on this signal, the controller 168 can power on the desorption component 142 to commence heating of the probe portion 124.

In implementations, the procedure 1000 can include directing the desorbed analytes from the sealed volume into the vacuum chamber of the analytical instrument system (block 1008). The vacuum chamber 154 of the analytical instrument system (e.g., mass spectrometer) 152 is connected to the sealed volume 144 of the pressure vessel (e.g., load lock) 132. As mentioned above, in the implementation shown in FIG. 1B, if the pressure vessel is configured to have a slight pressure leak, the gaseous pressure within the sealed volume 144 can be pumped down to just slightly higher than the gaseous pressure within the vacuum chamber 154. Once heating of the probe portion 124 begins, this pressure differential can facilitate the flow of desorbed analytes from the sealed volume 144 of the pressure vessel 132 into the vacuum chamber 154 of the analytical instrument system 152. Further, by having the desorption component 142 located in close proximity to outlet port 136 of the pressure vessel 132, efficiency of transfer of the desorbed analytes from the pressure vessel 132 to the analytical instrument system 152 is promoted. Still further, selection of the extracting phase material 130 can promote efficient transfer of the desorbed analytes from the pressure vessel 132 to the analytical instrument 152. For example, selecting extracting phase material 130 from which desorption of analytes does not occur under the above-described pump-down conditions, but from which desorption of analytes does occur during heating of the probe portion 124 by the desorption component 142 can promote efficient transfer of desorbed analytes from the pressure vessel 132 to the analytical instrument 152.

In implementations, prior to connecting the pump system (e.g., vacuum pump(s)) to the pressure vessel (e.g., load lock), the procedure 1000 can include cooling the probe portion (e.g., fiber) (block 1010). For example, when the analytes which are adsorbed onto and/or absorbed into the extracting phase material 130 include high volatility analytes, the analytes could potentially be desorbed (e.g., released) from the probe portion (e.g., SPME fiber) 124 prematurely, such as during pump-down of the pressure vessel 132 (e.g., during the process of reducing the pressure within the sealed volume of the load lock to near vacuum pressure by the vacuum pump(s)). Cooling the probe portion (e.g., SPME fiber) 124 prior to pump-down can counteract and/or prevent the possibility of analyte desorption prior to a desired pressure being established within the sealed volume 144 of the pressure vessel 132. The desorption component 142 can be configured with a cooling element (e.g., a fan) for cooling the probe portion 124.

As mentioned above, the sample analysis system implementations described herein allow for analyte desorption from an extracting phase material 130 coated on a probe portion (e.g., SPME fiber) of a SPME assembly 104 to occur in a partial vacuum (e.g., under a gaseous pressure substantially lower than atmospheric pressure), rather than at atmospheric pressure. Further, the sample analysis system implementations described herein achieve this by using the pressure vessel (e.g., a vacuum load lock) 132 for bringing the sample from atmospheric pressure to a pressure which is both substantially lower than atmospheric pressure and proximal to a gaseous pressure of a vacuum chamber 154 of an analytical instrument system (e.g., mass spectrometer) 152 to prepare the sample for introduction into the analytical instrument system. Desorbed analytes of the sample are then directed from the pressure vessel 132 into the analytical instrument system 152, which provides an output (e.g., mass spectra) providing information about the analytes. The sample analysis system implementations described herein promote efficient sample analysis. For example, the time elapsed from the time the probe portion (e.g., SPME fiber) 124 is introduced into the pressure vessel (e.g., load lock) 132 until the time the output (e.g., mass spectra) is provided by the analytical instrument system (e.g., mass spectrometer) 152 can be less than twenty seconds. Further, the vacuum tight connection between the SPME assembly 104 and the pressure vessel 132 promotes an efficient workflow. The sample analysis system implementations described herein promote analytical sensitivity. For example, by using the herein-described pressure vessel (e.g., vacuum load lock) 132 to prepare the sample for introduction into the analytical instrument system 152 (e.g., mass spectrometry system), the sample analysis system implementations described herein allow for analysis of less volatile chemicals, such as drugs and explosives.

Although the subject matter has been described in language specific to structural features and/or methodological acts, it is to be understood that the subject matter defined in the appended claims is not necessarily limited to the specific features or acts described. Although various configurations are discussed the apparatus, systems, subsystems, components and so forth can be constructed in a variety of ways without departing from this disclosure. Rather, the specific features and acts are disclosed as example forms of implementing the claims.

What is claimed is:
1. A sample introduction system, comprising:
a pressure vessel having an enclosure forming a sealed volume;
an inlet port connected to the enclosure, the inlet port configured to receive a probe portion of a solid phase micro extraction assembly into the sealed volume, the probe portion being coated with an extracting phase material, the analyte being at least one of adsorbed onto or absorbed into the extracting phase material;

an outlet port connected to the enclosure and connected to a vacuum chamber of an analytical instrument system, where the enclosure and the analytical instrument system are separated by a valve; and a desorption apparatus located within the sealed volume, the desorption apparatus configured to heat the analyte for causing desorption of the analyte from the extracting phase material.

2. The sample introduction system as recited in claim 1, wherein the pressure vessel comprises a load lock.

3. The sample introduction system as recited in claim 1, wherein the pressure vessel is configured to be connected to a vacuum for establishing a gaseous pressure within the sealed volume, the gaseous pressure being substantially less than atmospheric pressure.

4. The sample introduction system as recited in claim 3, wherein the vacuum is generated by a vacuum pump.

5. The sample introduction system as recited in claim 3, further comprising a pressure sensor configured to detect the gaseous pressure within the sealed volume.

6. The sample introduction system as recited in claim 1, wherein the analytical instrument system comprises a mass spectrometer.

7. The sample introduction system as recited in claim 1, wherein a desorbed analyte is directed via the outlet port of the pressure vessel into the vacuum chamber.

8. The sample introduction system as recited in claim 1, wherein the inlet port is configured to be connected to the solid phase micro extraction assembly via a sealed connection.

9. The sample introduction system as recited in claim 1, wherein the desorption apparatus is configured to commence heating of the analyte for causing desorption of the analyte when a gaseous pressure within the sealed volume is substantially less than atmospheric pressure.

10. A sample analysis system, comprising:
a vacuum chamber; and
a pressure vessel connected to the vacuum chamber, the pressure vessel comprising:
   an enclosure forming a sealed volume;
   an inlet port connected to the enclosure, the pressure vessel configured for receiving a probe portion of a solid phase micro extraction assembly into the sealed volume via the inlet port, the probe portion being coated with extracting phase material and analytes, the analytes being at least one of absorbed into or adsorbed onto the extracting phase material;
   an outlet port connected to the enclosure, the outlet port connecting the pressure vessel to the vacuum chamber, where a valve separates the pressure vessel and the vacuum chamber; and
   a desorption apparatus located within the sealed volume, the desorption apparatus configured for heating the probe portion for causing desorption of the analytes from the extracting phase material,
wherein heating the probe portion commences when a gaseous pressure within the sealed volume of the pressure vessel is established at a first pressure, the first pressure being substantially less than atmospheric pressure, the desorbed analytes being directed from the pressure vessel into the vacuum chamber via the outlet port.

11. The sample analysis system of claim 10, wherein the pressure vessel comprises a load lock.

12. The sample analysis system of claim 10, wherein a gaseous pressure within the vacuum chamber is at a second pressure, the second pressure being less than the first pressure.

13. The sample analysis system of claim 12, wherein the pressure vessel and the vacuum chamber are configured for being connected to a vacuum pump system for establishing the pressure vessel at the first pressure and for establishing the vacuum chamber at the second pressure.

14. The sample analysis system of claim 13, wherein the pressure vessel comprises a pressure sensor.

* * * * *